United States Patent [19]

Filhol

[11] 4,451,237
[45] May 29, 1984

[54] DENTAL ANCHORING MEANS

[76] Inventor: Stuart J. Filhol, Castlefreke, County Cork, Ireland

[21] Appl. No.: 337,403

[22] Filed: Jan. 6, 1982

[51] Int. Cl.³ .............................................. A61C 5/04
[52] U.S. Cl. ..................................... 433/225; 433/165
[58] Field of Search ................................. 433/225, 165

[56] References Cited

U.S. PATENT DOCUMENTS

| 1,809,553 | 6/1931 | Graul | 279/93 |
| 3,751,176 | 8/1973 | Hollen | 433/165 |
| 4,035,100 | 7/1977 | Kruger et al. | 408/226 |

FOREIGN PATENT DOCUMENTS

| 40425 | 3/1932 | France | 433/165 |

OTHER PUBLICATIONS

"Link Series" Prosthetic Dentistry Magazine, May 1979 vol. 41 No. 5.

Primary Examiner—Robert Peshock
Attorney, Agent, or Firm—Gifford, VanOphem, Sheridan & Sprinkle

[57] ABSTRACT

Dental anchoring means of the kind including a threaded pin which is located in a hole in a tooth.

Before insertion into the hole, the pin is integral with a shank through a neck which allows the pin to break off from the shank after insertion.

The pin and shank are located in a longitudinal open-ended bore in a connecting member which is arranged to be secured in a dental handpiece.

The pin and shank are fixed in the bore by forming an enlarged head on the shank which is a force fit in the bore. This locks the pin and shank securely in the bore during use and the connecting member can be of different material from the shank and pin.

6 Claims, 1 Drawing Figure

U.S. Patent    May 29, 1984    4,451,237
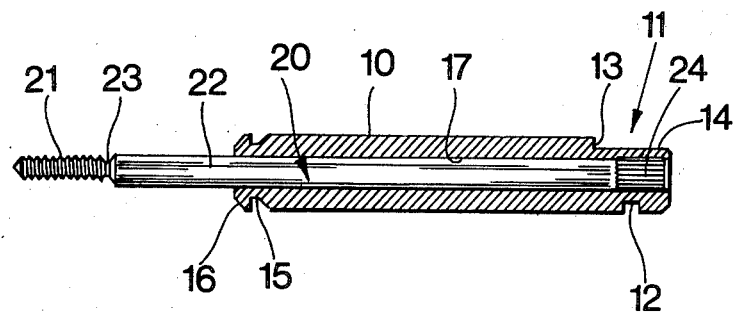

DENTAL ANCHORING MEANS

This invention relates to dental anchoring means and in particular to dental anchoring pins for insertion into teeth.

Dental anchoring pins have been proposed for use in anchoring built up superstructures onto teeth. In some cases, see for example British Pat. No. 1,347,226, a dental pin has been attached to a shank through a neck portion, the shank being arranged for location in a connecting member securable in a handpiece which drives the pin into the tooth and breaks off the pin from the shank at the neck after insertion. In other cases, the pin and shank have been integral with the connecting member, see for example British Pat. No. 1,482,681. In the latter case the shank and connecting member are discarded after the pin has been inserted into the tooth and detached from the shank. When the pin and shank have to be inserted into a separate connecting member before location in the handpiece there has been a risk that the pin and shank may fall out of the connecting member during insertion of the pin in the tooth and this is, of course, hazardous to the patient.

When an integral construction is employed, the pin, shank and connecting member are formed of the same material so that if expensive material is desired to be used for the dental pin portion, the shank and connecting member become an expensive item to be discarded.

An object of the present invention is to provide dental anchoring means in which the pin material may be different from the material of the connecting member and in which it is virtually impossible for the pin and associated shank to become inadvertently detached from the connecting member during insertion of the pin.

According to the invention, dental anchoring means comprises a threaded pin for insertion into a preformed hole in a tooth, a shank integral with the pin, a neck intermediate the pin and the shank whereby the pin is detached from the shank after insertion in said hole, and a connecting member including latching means for locating the member in a handpiece by which the pin is rotated in the hole, the connecting member having an open-ended bore extending longitudinally thereof and the pin and shank being located in the bore so that the pin projects from one end of the bore and at least a portion of the shank is located in the bore, said portion of the shank including fixing means which in use prevents the shank from passing along the bore towards the end of the bore from which the pin projects.

Conveniently the fixing means is in the form of a portion of the shank of enlarged section which is a force fit in the bore and the portion of enlarged section has longitudinal external splines or knurls which when engaged in the bore form corresponding grooves in the wall of the bore.

Preferably the connecting member and the pin and shank are assembled by passing the pin and shank through the longitudinal bore until the threaded pin projects from the end of the bore and the enlarged section is forced along the bore to engage the walls of the bore to be secured therein.

Conveniently the shank and pin are formed of one metal and the connecting member is formed of another metal.

In one embodiment the connecting member is formed of brass or the like and the pin and shank are formed of titanium or stainless steel.

The pin and shank may be inserted in the longitudinal bore by a punch which engages the shank and forces it along the bore, the enlarged section deforming the bore as it passes therealong Further features of the invention will appear from the following description of an embodiment of the invention given by way of example only and with reference to the drawing which is a longitudinal section through an assembled connecting member and pin member.

Referring to the drawing a connecting member 10 is in the form of a tubular member having an outer cylindrical surface in one end of which is machined latching means 11 of conventional form for location in a dental handpiece. The latching means includes a part-circular groove 12 and a recess 13 defining a flat 14. At the other end of the member 10 is formed a circumferential groove 15 and a taper 16.

Extending longitudinally and coaxially of the member 10 from one end to the other is a circular bore 17. Within the bore 17 is secured a dental pin member 20 having at one end a threaded pin portion 21 which is the portion to be located in a tooth. The threaded portion 21 is integral with a cylindrical shank portion 22 and a frangible neck portion 23 is interposed between the threaded pin portion 21 and the cylindrical shank portion 22 to provide a break-off point when the threaded portion 21 has been screwed into a preformed hole in the tooth, in known manner.

At the free end of the shank portion 22 remote from the threaded pin portion 21 is formed a portion 24 of enlarged section as, for example, by knurling or providing splines, such that the enlarged section is greater in cross section than the nominal diameter of the bore 17. The pin member 20 is located in the connecting member 10 by inserting the pin member 20, threaded pin portion 21 first, along the bore 17 from the end of the member 10 at which the latching means 11 is located. To achieve such insertion the pin member 20 is conveniently urged along the bore 17 by a punch engaging the end 24 of the shank portion 22. When the enlarged section 24 engages the walls of the bore such walls are slightly deformed, such as, for example, to form grooves corresponding to the splines, and a secure location of the pin in the member is achieved. In the case where the free end of the shank portion has longitudinal splines forming grooves in the wall of the bore this ensures that relative rotation between the two members is prevented.

In the illustrated arrangement the portion 24 is at the free end of the shank portion which is selected to be of a length that such portion lies close to the end of the bore 17, but to save of the amount of discarded metal in the shank portion 22 this may be shorter and the end with the enlarged portion 24 may be pushed further along the bore 17 from the open upper end. Thus in the case of pins made from expensive materials, such as titanium, the shank portion 22 will occupy a relatively short length of the bore 17 after insertion, whereas for relatively less expensive materials, such as stainless steel, the shank portion 22 may occupy a greater length of the bore.

Conveniently the connecting member 10 is formed from brass tube and is discarded with the shank portion 22 when the pin 20 has been inserted in a tooth.

Alternatively after the pin portion 21 has been detached from the shank portion 22 the shank portion 22 is pushed back up the bore 17 for removal from the bore 17 and a further integral pin and shank are inserted into the bore from the end of the member 10 having the latching means 11.

The shank portion 22 may have a diameter, apart from the enlarged portion 24, which is less than that of the bore 17 so that there is some play between the bore 17 and the portion 22 and the shank portion 22 can be angled relative to the axis of the connecting portion 10.

The dental anchoring means described provides an assembly in which the dental pin member is securely located in use in the connecting member while allowing the pin member to be made of a different material to the shank. It is easily and economically made and is usable with conventional dental handpieces.

What I claim as my invention and desire to secure by Letters Patent of the U.S. is:

1. Dental anchoring means comprising a threaded pin for insertion into a preformed hole in a tooth, a shank integral with the pin, a neck intermediate the pin and the shank whereby the pin is detached from the shank after insertion in said hole, and a connecting member including latching means at one end thereof for locating the member in a handpiece by which the pin is rotated in said hole, the connecting member having an open-ended bore extending longitudinally thereof and a portion of the shank being located in the bore, said portion being, along at least part of its length, of enlarged section to define fixing means which provide a force fit between the enlarged section and the bore when the shank and pin are inserted along the bore from the end of the bore adjacent the latching means with the pin projecting from the opposite end of the bore, and in use the fixing means preventing the shank from passing along the bore towards the end of the bore from which the pin projects and preventing relative rotation between the shank and connecting member.

2. Dental anchoring means according to claim 1 wherein the fixing means is located at the free end of the shank remote from the pin.

3. Dental anchoring means according to claim 1 wherein the fixing means is engaged with an end portion of the bore remote from the end of the bore from which the pin projects.

4. Dental anchoring means according to claim 1 wherein the shank and pin are formed of one metal and the connecting member is formed of another metal.

5. Dental anchoring means according to claim 1 wherein the connecting member is generally cylindrical and the bore is of circular cross-section and extends coaxially of the member.

6. Dental anchoring means according to claim 1 wherein the external diameter of the shank is slightly less than the diameter of the bore, except at the location of said fixing means, to allow some play between said bore and the shank.

* * * * *

UNITED STATES PATENT AND TRADEMARK OFFICE
CERTIFICATE OF CORRECTION

PATENT NO. : 4,451,237
DATED : May 29, 1984
INVENTOR(S) : Stuart J. Filhol

It is certified that error appears in the above—identified patent and that said Letters Patent is hereby corrected as shown below:

Cover page, column 1, after "Filed: Jan. 6, 1982", insert

--Foreign Application Priority Data - Jan. 6, 1981

[GB] United Kingdom...........8100239--

Signed and Sealed this

Twenty-third Day of October 1984

[SEAL]

Attest:

GERALD J. MOSSINGHOFF

*Attesting Officer*        *Commissioner of Patents and Trademarks*